United States Patent [19]

Wiesner

[11] Patent Number: 4,505,154

[45] Date of Patent: Mar. 19, 1985

[54] CONTACTLESS MEASURING DEVICE FOR REAL-TIME DETECTION OF THE PROPERTIES AND QUANTITIES RESPECTIVELY CHARACTERISTIC OF THE SEPARATION OF VOLUMES OF LIQUID AND THE SPLITTING OF LAYERS OF LIQUID IN THE NIPS FORMED BY THE ROLLERS ON PRINTING MACHINES

[75] Inventor: Reiner Wiesner, Weiterstadt, Fed. Rep. of Germany

[73] Assignee: Forschungsgesellschaft Druckmaschinen e.V., Franfurt am Main, Fed. Rep. of Germany

[21] Appl. No.: 465,209

[22] Filed: Feb. 9, 1983

[30] Foreign Application Priority Data

Feb. 19, 1982 [DE] Fed. Rep. of Germany ....... 3205941

[51] Int. Cl.³ .............................................. B41F 7/24
[52] U.S. Cl. .................. 73/150 R; 73/64 A; 73/54; 101/148
[58] Field of Search ............... 73/150 R, 590, 592, 73/658, 61.1 R, 54; 101/365, 350, 349, 348

[56] References Cited

U.S. PATENT DOCUMENTS

| 2,993,371 | 7/1961 | Greubel | 73/150 R |
| 3,368,399 | 2/1968 | Wirz | 73/150 R |
| 3,439,175 | 4/1969 | Kammuller et al. | 250/218 |
| 3,869,984 | 3/1975 | Toth | 73/150 R |
| 3,960,451 | 6/1976 | Wirz et al. | 356/161 |
| 4,332,161 | 6/1982 | Kakino | 73/104 |

Primary Examiner—Gerald Goldberg
Assistant Examiner—Hezron Williams
Attorney, Agent, or Firm—Leydig, Voit, Osann, Mayer & Holt, Ltd.

[57] ABSTRACT

This invention relates to a method of and a device for the weighted measurement of quantities of liquid per unit area and/or the relative quantities of a liquid per unit area by means of an acoustic sensor. More particularly, the method permits the measurement of quantities of liquid and/or relative quantities of a liquid per unit area at the outlet of a nip formed by two rollers completely or partially covered by the liquid and/or liquid mixture concerned, the rollers rolling one upon the other and the layer of liquid in the nip being split at the nip outlet. Splitting of the layer of liquid occurs particularly in printing machines and glue applying machines, to which the invention can accordingly be applied.

20 Claims, 4 Drawing Figures

CONTACTLESS MEASURING DEVICE FOR REAL-TIME DETECTION OF THE PROPERTIES AND QUANTITIES RESPECTIVELY CHARACTERISTIC OF THE SEPARATION OF VOLUMES OF LIQUID AND THE SPLITTING OF LAYERS OF LIQUID IN THE NIPS FORMED BY THE ROLLERS ON PRINTING MACHINES

The invention relates to a contactless measuring method and device for the real-time detection of the properties and quantities respectively characteristic of the separation process in respect of volumes of liquid and the splitting process in respect of layers of liquids.

The invention permits the weighted measurement of the amount of damping medium per unit area, the damping medium remaining on the surface of the ink having a greater weighting than the damping medium emulsified in the ink.

OBJECT OF THE INVENTION

The separation of volumes of liquid and the splitting of layers of liquid are technically generally intended to produce smaller volumes of liquid and thinner layers of liquid of a defined size and thickness respectively. The method according to the invention can be used in these conditions for monitoring and control units for real-time measurement in the corresponding machines. Particularly when materials are printed, e.g. as when paper is printed with printing ink, the quality of the print is very dependent upon the thickness of the layer of ink applied. Also, in offset printing, the quality of the print and undisturbed operation of the printing process are very dependent upon the quantity of damping medium and the ratio between the quantities of ink and damping medium at the outlet of the nip formed between inking rollers and the printing plate cylinder. The damping medium remaining on the surface of the ink has a greater weighting in these relationships than the damping medium emulsified in the ink, and also has a greater influence on the sonic waves emitted by the nip outlet and detected by the acoustic sensor than the damping medium emulsified in the ink, so that the method according to the invention is particularly suitable for function and quality monitoring in this printing method.

STATE OF THE ART

At the present time, electrical, magnetic and spectral measuring methods are mainly used for the real-time detection of the separation of volumes of liquid into sub-volumes of a specific size and for the splitting of layers of liquid into sub-layers of specific thickness, without interfering physically with the process. The first group includes primarily capacitance and conductivity measuring devices while the second group includes primarily inductive pick-offs while the third group includes measuring devices operating on the basis of microwaves, infrared radiation, visible light, ultraviolet radiation, X-radiation and nuclear radiation. The echo-sounding method should also be mentioned in respect of the detection of relatively large volumes and relatively thick layers.

In all the measuring devices hitherto used in offset printing for monitoring damping medium supply without physically interfering with the process, a transmitter emits energy in the form of electromagnetic waves through the ink carrying the damping medium and, given suitable wavelengths, the proportion of the emitted energy absorbed by the damping medium is indicated by a detector. Apart from the radioactive tracer method which has hitherto only been used in the laboratory, the thickness of the layer of ink in printing machines has also been measured by contactless methods.

COMMENTARY ON THE PRIOR ART

The real-time measuring methods hitherto used without physically interfering in the process, for the detection of the separation of volumes of liquid into sub-volumes according to their size and the splitting of layers of liquid into sub-layers according to the layer thickness require, in addition to a signal receiver, a signal transmitter independent of the separation and splitting processes, while in the method according to the invention the separation and splitting processes themselves perform the transmission function and the mechanical waves emitted during the mechanical separation and splitting processes are detected.

Those measuring processes which do not physically interfere with the process and which are used more particularly in offset printing for monitoring the damping medium supply also have the particular disadvantage that they measure the total quantity of damping medium and do not permit greater weighting of the amount of damping medium remaining on the ink surface as compared with the amount of damping medium emulsified in the ink, in keeping with its greater influence on the functioning of this printing process. In addition, although considerable attempts have been made, the measuring devices available at the present time for damping medium monitoring have not been capable of miniaturization to an extent such that their incorporation in offset printing machines can be regarded as a simple matter and, in particular, it is impossible to obtain a free choice in respect of the measuring site between the rollers. In these damping medium monitors, a surface element of the printing plate cylinder between the damping unit and the inking unit is generally chosen as the measuring site, but this is only possible if the damping unit directly touches the printing plate cylinder and not, as in some offset printing machines, is in direct contact only with the inking unit. In addition, an apparently adequate amount of damping medium on a surface element not intended to receive ink is no guarantee that such surface elements will not actually receive ink due to intensive evaporation of the damping medium and excessive pressure in the nips between the inking rollers and the plate cylinder. Conversely, in respect of those surface elements that are intended to receive ink, it provides no guarantee that there will not be inadequate acceptance of ink due to inadequate pressure in the nips between the inking rollers and the plate cylinder and the resulting incomplete displacement of the damping medium by the ink.

Since such disturbances in the processes fundamental to the functioning of the offset printing process, i.e. the splitting of the film of damping medium on those surface elements which are not intended to receive ink and the splitting of the ink and damping medium emulsion on those surface elements that are intended to receive the ink, have a considerable influence on the sonic waves emitted in the splitting process, the method according to the invention detects these disturbances directly where they arise and hence with practically no time delay.

The known contactless methods of measuring the thicknesses of layers of ink as used in printing machines are all dependent relatively considerably on different physical properties of the roller materials on which the printing ink is situated. Their use is therefore restricted to the use of specific roller materials suitable for the particular measuring method. For example, capacitative measuring methods are restricted to metal roller surfaces or roller materials whose dielectric constant differs considerably from the dielectric constants of the ink. Ink layer thickness measuring devices operating with visible light react with undesirable sensitivity to variations in the reflectance of the roller surfaces, and these are inevitable in the practical operation of printing machines.

In contrast, the method according to the invention allows ink layer thickness measurement practically completely unaffected by the roller material, on the assumption that the ink layer in the roller nip is divided up in a known ratio at the nip outlet and no damping medium is present. Particularly in the offset printing process, which is characterised by the presence of a damping medium in emulsified form adhering to the surface of the ink, the measuring method according to the invention can be used as an ink layer thickness measuring method only conditionally, but since any increase or decrease in the thickness of the layer of ink entails an increase and fall-off in the proportion of damping medium emulsified in the ink in comparison with the proportion of damping medium adhering to the ink surface, the different influence of these two damping medium fractions on the sonic waves emitted in the splitting process has the effect that the weighted measurement in respect of the quantities of damping medium also provides information on the thickness of the ink layer.

PROBLEM

The problem with which the invention is concerned is to develop a measuring method which is characteristic of and quantitatively provides contactless real-time detection of the separation and splitting of volumes of liquid into sub-volumes, does not influence the separation and splitting process and can be used for monitoring and controlling such processes.

SOLUTION

According to the invention, to solve this problem, the sonic waves arising and emitted in the separation and splitting of volumes of liquid into sub-volumes are received by an acoustic sensor disposed near the separation and splitting site and are further processed and displayed electronically. Since the properties of the liquid or the constituents of a mixture of liquids characteristic of the separation and splitting process, e.g. viscosity, elasticity, interfacial tension or, generally, the consistency resulting from the interactions of the molecules, also characterise the sonic waves arising in these conditions, the method according to the invention solves the problem of providing quantitative real-time contactless measurement of a quantity characterising the separation and splitting process and can therefore be used in monitoring and controlling such processes. More particularly, in the separating and splitting process at the outlet of the nip formed between two rollers or roller segments running one upon the other and completely or partially covered with the liquid or liquid mixture concerned, the measuring method according to the invention can be so calibrated by means of other measuring methods that the quantities of liquid or relative quantities of liquid can be displayed directly. In the borderline case, in which the radius of the roller can be regarded as infinitely large, the same applies in respect of a roller running on a plate, and in the borderline case in which the radii of both rollers can be regarded as infinite, the same applies in respect of the unilaterally caused lifting of one plate from the other.

Particularly in the case of the splitting of ink in printing machines and the splitting of glue in glue application machines, it is possible, by means of known layer thickness measuring methods, to calibrate the method according to the invention in such a manner that it can be used as an ink and glue layer thickness measuring method for monitoring and controlling these layer thicknesses. Since, in the offset printing process, the damping medium in the mixture of printing ink and damping medium in the roller nip has a viscosity lower by a factor of $10^{-3}$ than the printing ink, this mixture is split at the nip outlet mainly transversely by volume elements containing damping medium, i.e. the splitting occurs at the weakest points, so that the damping medium reaches the ink surface where its influence is greatest on the next splitting operation. The work required for this and the energy emitted in these conditions in the form of sonic waves varies very considerably with a variation of the relative quantities of these two fractions because of the considerable difference between the consistency of the ink and the consistency of the damping medium. The vibrations of the ink lamellae and ink filaments, which cause the sonic radiation, are also greatly attenuated by the emulsified damping medium droplets and the damping medium remaining on the surface of the ink, the attenuation varying with the relative proportions of ink and damping medium.

Measurement, by means of an acoustic sensor, to detect the sound emitted during the separation of a mixture of printing ink and damping medium thus solves the problem of finding and measuring a quantity in which the amount of damping medium remaining on the surface of the ink is included with greater weighting than the amount of damping medium emulsified in the ink, and which additionally contains information as to the amount of ink. More particularly, this solves the problem of detecting directly at the site where they occur, and hence without any time delay, disturbances to the offset printing process functioning and hence variations in printing quality produced by disturbed splitting behavior due to inadequate or excessive damping medium supply or excessive or inadequate pressure between the inking rollers and the printing cylinder, e.g. "tinting" or "water marks". Measurement of the splitting noise at the first inking roller thus has the particular advantage that the liquid distribution can be detected directly on the plate.

The invention can therefore be used for the contactless real-time detection of the relative proportions of ink and damping medium, which are relevant to the offset printing process, with special weighting of the amount of damping medium remaining on the surface of the ink after the splitting operation, and is suitable for use in monitoring and controlling this ratio and hence the print quality. The acoustic sensor is also miniaturizable to an extent such that it is possible to instal it even in very restricted spaces.

The principle of the invention is applicable generally to the contactless measurement of quantities of liquid, liquid being applied between two opposite surfaces, the surfaces being moved apart, the sonic waves which arise and are emitted during this splitting process being received by an acoustic sensor and the received energy being evaluated by measurement.

The method can be used particularly for measuring vapour (e.g. water vapour) in gases (e.g. air), the acoustic sensor measuring the emitted sound which occurs in the nip between two rollers or roller segments as they roll one upon the other and are covered with materials which absorb these vapours (e.g. a hygroscopic layer).

ADVANTAGES OF THE INVENTION

The advantages that can be attained with the invention are, in particular, that the, microscopically considered, mechanical process of separation and splitting of a volume of liquid into sub-volumes is detected without contact by the resulting and emitted mechanical waves by measurement using an acoustic sensor. The properties of the liquid or liquid mixture characteristic of the separating and splitting process also characterise the sonic waves arising and emitted in these conditions. Detection of these sonic waves by measurement therefore provides a yardstick which is a direct characteristic of the separation and splitting process and which can be used for monitoring and controlling these processes. In the method according to the invention, the separating and splitting process itself performs the transmission function and it therefore has a considerable advantage over the measuring methods previously used to detect these processes. The method according to the invention can be so calibrated that it directly displays the sub-volume size or sub-volume size distribution.

The invention can be used particularly as a layer thickness measuring method in respect of the splitting of a volume of liquid at the outlet of the nip formed between two rollers or roller segments rolling one upon the other as in printing machines and glue application machines, and compared with the known layer thickness measurement methods it has the advantage that it detects the layer thicknesses without contact while being practically unaffected by the roller material and requires no transmitter independent of the process. It is therefore usable for monitoring and controlling liquid layer thicknesses in such splitting processes.

In comparison with the measuring methods hitherto used particularly in the offset printing process for contactless monitoring of the damping medium supply, the invention has the advantage that, instead of detecting the total quantity of damping medium, it detects a quantity characteristic of the splitting of the printing ink and damping medium mixture, and this quantity includes the relative proportions of the printing ink and damping medium with particular weighting of the proportion of damping medium remaining on the ink surface after the splitting process. Since the acoustic sensor in the method according to the invention is miniaturizable to an extent such that the measuring site in the offset printing machine can be freely selected, it also has the advantage that splitting of the mixture of printing ink and damping medium can be detected in real-time without contact directly at the outlets of the nips between the inking rollers and the printing plate cylinder, i.e. at the sites where the best-known malfunctions occur to the offset printing process. Since the method according to the invention can also be used when the damping unit contacts the inking unit instead of the printing plate, this method is of use in all known offset printing machines for the purpose of detecting, monitoring and controlling the weighted relative proportions of printing ink and damping medium.

Exemplified embodiments are explained hereinafter with reference to the drawings, wherein:

FIG. 1 is a detail of an offset printing machine with an inking and damping unit.

FIG. 2 illustrates a measuring system.

FIG. 3 is a graph of the measured value against time and

FIG. 4 shows a different type of measuring system.

Figure 2:
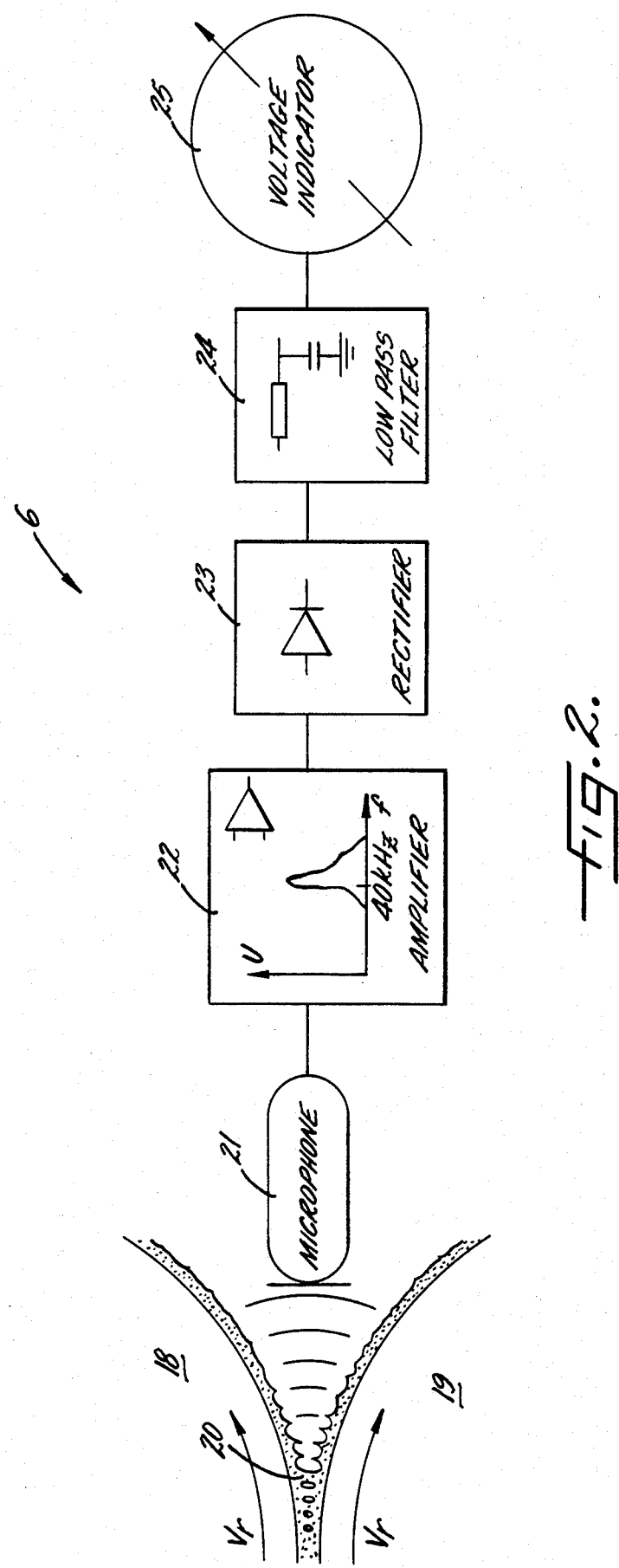

The first exemplified embodiment of the invention to be described here is illustrated in FIG. 2.

Referring to FIG. 2, reference 20 denotes the outlet of the nip formed by two rolls 18, 19 rolling one upon the other at the circumferential speed $v_r$, the outer surfaces of the rollers being covered with a liquid mixture which splits at the nip outlet. The acoustic sensor 6 intended for detecting the sonic signals emitted in the splitting process is situated opposite the nip outlet. Integer 21 of the sensor 6 is an ultrasonic crystal microphone which converts the received sonic signals into electrical signals which are then amplified in amplifier 22. Integer 22 also illustrates the frequency curve (amplitude U as a function of frequency f) of the unit formed by the crystal microphone and the amplifier, this curve having a resonant peak at a sonic frequency of 40 kHz, and affording the advantage that the influence of disturbing machine noise of a frequency distinctly below 40 kHz was largely eliminated. The amplifier output signal is fed to the rectifier shown in integer 23, which converts the incoming bipolar signal train into a unipolar signal train. The rectifier 23 is followed by a low-pass frequency filter shown at integer 24, which converts the high-frequency unipolar signal train to a low-frequency signal by averaging. The low-frequency signal is then displayed by a voltage indicator shown at integer 25.

Figure 3:
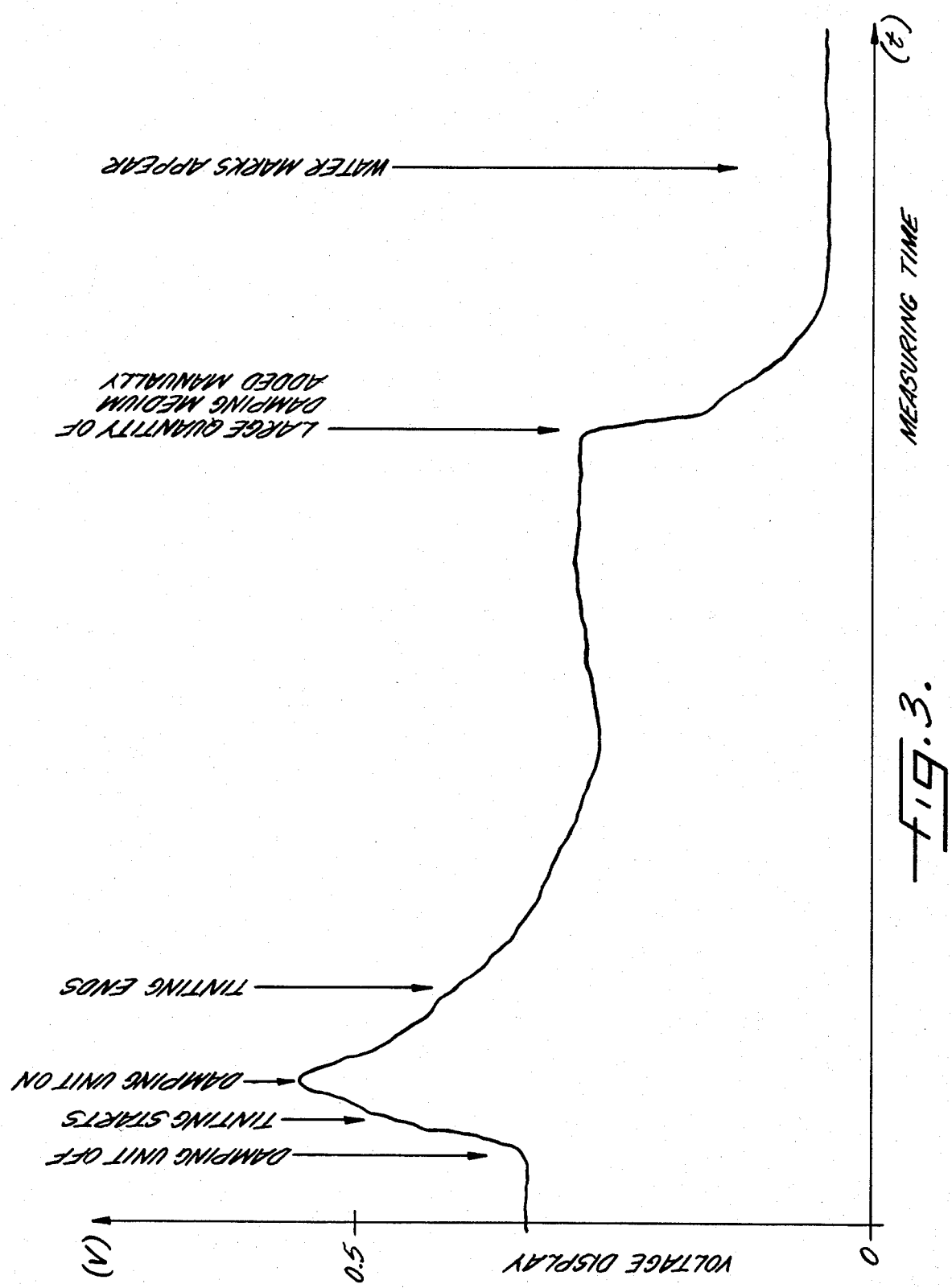

FIG. 3 illustrates the voltage display recorded by an xt-recorder against the measuring time as obtained with the acoustic sensor shown in FIG. 2 used for measurements in a sheet-fed offset press with variations in the printing conditions. In this case the acoustic sensor was disposed opposite the nip outlet between the first inking roller following the damping unit in the direction of rotation and the distributor roller situated thereabove.

Referring to FIG. 3, proceeding from left to right it will be seen how, starting from normal printing conditions, the voltage display increases greatly after the supply of damping medium has been stopped and tinting occurs after a relatively short time equivalent to the printing of seven sheets, tinting being the term used to denote an offset printing malfunction in which those surface elements of the printing plate which are not intended to accept ink are no longer protected against so doing by the film of damping agent and therefore accept ink. Re-starting of the damping medium supply just after this malfunction was observed results in the voltage display falling off and normal printing conditions being resumed. A spray was then used to apply a very considerable amount of damping agent to the damping rollers, again starting from normal printing conditions, the damping medium thus being transferred to the plate cylinder and resulting in a considerable fall-off in the voltage display. It was not until after a relatively considerable time following the fall-off in the voltage display—a factor associated with the fact that the ink in the inking unit has the capacity to store damping medium, that water marks appeared on the print, this being an offset printing process malfunction in which those surface elements of the printing plate which are intended to accept the ink are inked only incompletely because of the high proportion of damping medium on the surface of the ink. Because of the excessive damping medium feed, the splitting of the printing ink and damping medium emulsion occurring between said printing plate surface elements and the inking rollers under normal printing conditions was replaced by splitting of the damping medium adhering to the surface of the ink, and in these conditions no ink can be transferred. The resumption of normal printing conditions required a very considerable amount of time after this intensive excess damping of the ink in the inking unit to the very limits of its damping medium storage capacity.

Figure 1:
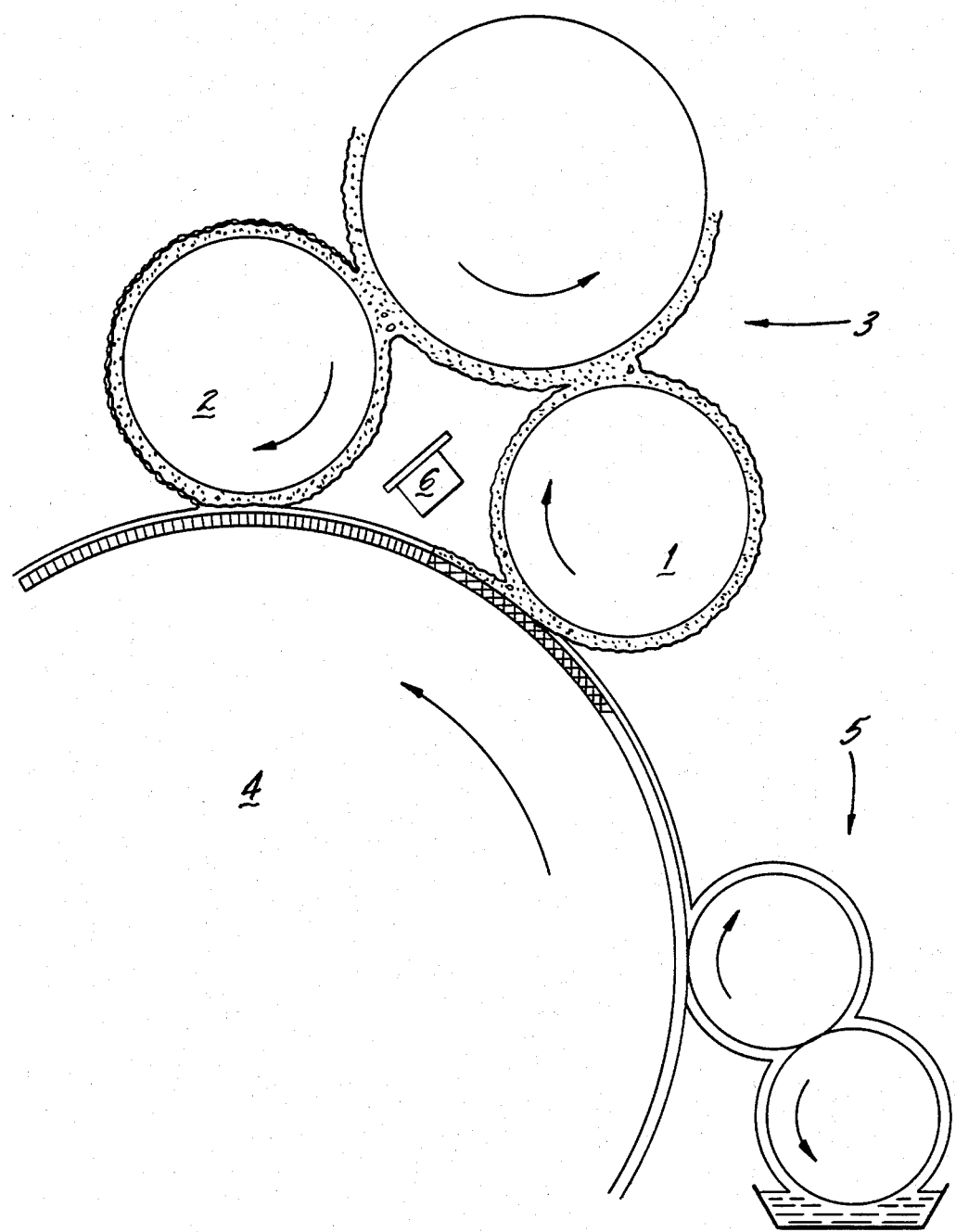
FIG. 1 illustrates a detail of a printing machine. The rollers 1, 2 of an inking unit 3, which is not shown in detail, roll on a plate cylinder 4. A damping unit 5 is associated with the plate cylinder 4 and is situated before the inking unit 3 as considered in the direction of rotation of the plate cylinder. The acoustic sensor 6, which is a basic feature of the invention, is disposed in the nip outlet between the plate cylinder 4 and the first inking roller 1.

The following results were obtained in a series of measurements carried out with the first exemplified embodiment of the invention shown in FIG. 1 on an experimental inking unit with separate variation of the thickness of the ink layer, the quantity of damping medium, and the speed:

(a) The ultrasonic level, i.e. the voltage display, falls off when the thickness of the layer of ink in the nip falls off and/or when the quantity of damping medium in the nip increases, i.e., when the (quantity of ink)/(quantity of damping medium)

ratio with respect to the unit area decreases.

A considerable decrease in this ratio results in water marks appearing in the print.

(b) The ultrasonic level, i.e. the voltage display, increases when the thickness of the layer of ink in the nip increases and/or when the quantity of damping medium in the nip increases, i.e. when the (quantity of ink)/(quantity of damping medium)

ratio with respect to the unit area increases. A considerable increase in this ratio results in tinting.

(c) The ultrasonic level increases only slightly when the circumferential speed of the rollers increases.

According to the results heretofore obtained with the first exemplified embodiment of the invention, it may be assumed that regulation of the flow of ink and damping medium to give a constant voltage display in this exemplified embodiment also results in the ratio of the quantity of ink to the quantity of damping medium remaining constant, the same applying particularly to the quantity of damping medium adhering to the surface of the ink. Consequently, if the voltage display is kept constant by regulating the flow of ink and damping medium, a constant offset printing quality will be obtained, disregarding possible changes in the quality of the material being printed, possible wear of the printing plate, and the like.

Figure 4:
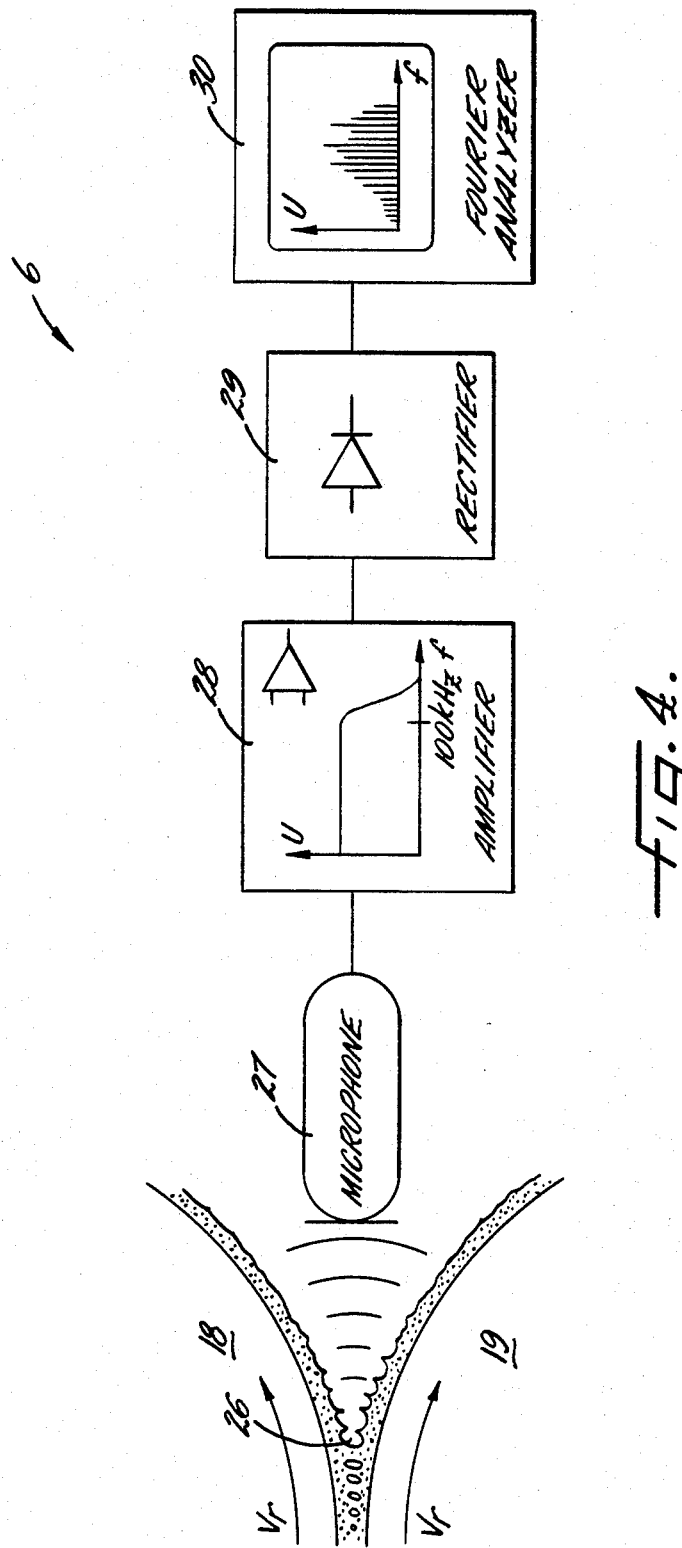

The second exemplified embodiment of the invention described hereinbelow is illustrated in FIG. 4.

Referring to FIG. 4, reference numeral 26 again denotes a nip outlet formed by two rollers rolling one upon the other at the circumferential speed $v_r$ and with their surfaces covered with a liquid mixture which splits at the nip outlet. The acoustic sensor is again situated opposite the nip outlet for detecting the sonic signals emitted during the splitting process. Integer 27 of the acoustic sensor again denotes a microphone which converts the received sonic signals into electrical signals which are then amplified in the amplifier shown at integer 28. The latter also shows the frequency curve of the unit formed by the microphone and the amplifier, this curve being so selected as to be particularly suitable for subsequent frequency-selective evaluation. The curve is flat up to approximately 100 KHz. The amplifier output signal is fed to the rectifier shown at integer 29, which converts the incoming bipolar signals to unipolar signals. The latter are then fed to the Fourier analyzer shown at 30, in which they are subjected to frequency-selective analysis, i.e., they are split into their Fourier components. Fourier analysis of the sound waves emitted by the nip permits more detailed information to be obtained concerning the splitting process and its influencing variables than the evaluation method illustrated in the first exemplified embodiment of the invention.

I claim:

1. A contactless measuring device for sensing splitting of a volume of liquid in a nip formed by rollers in a machine, said measuring device providing real-time detection of properties of the liquid that are characteristic of the process of said splitting such as viscosity, elasticity, interfacial tension and the like, said contactless measuring device commprising, in combination, acoustic sensing means disposed near the outlet of the nip for receiving sonic signals generated by the separation of the liquid in the nip and generating an electrical signal representative of the sonic signals, and electronic means for evaluating the electrical signal generated by the acoustic sensing means and for generating an electrical signal responsive to said evaluation indicating said properties of the liquid that are characteristic of said splitting process.

2. The combination as claimed in claim 1, further comprising means for displaying the electrical signal generated by the means of evaluating.

3. The combination as claimed in claim 1, further comprising means for adjusting the machine to change at least one of said properties of the liquid that are characteristic of the splitting process.

4. The combination as claimed in claim 1, wherein the nip is between an applicator roller and a printing plate in a printing machine.

5. The combination as claimed in claim 1, wherein the acoustic sensing means is substantially responsive to sonic signals only in the ultrasonic range.

6. The combination as claimed in claim 1, wherein the electronic evaluator comprises a Fourier analyzer.

7. The combination as claimed in claim 1, wherein the electronic evaluating means comprise rectifier means for converting the electronic signal, representative of the sonic signals, in bipolar form to a unipolar signal.

8. The combination as claimed in claim 7, further comprising means for performing a frequency-selective analysis of the unipolar signal to generate the electrical signal indicating the properties and quantity respectively characteristic of the separation of the volume of liquid and the splitting of layers of the liquid in the nip.

9. The combination as claimed in claim 3 wherein the means for performing the frequency-selective analysis comprise a Fourier analyzer.

10. In an offset printing machine of the type wherein a combination of printing ink and dampening medium passes through and is split at a nip, the print quality being affected by the ratio of the quantity of ink to the quantity of dampening medium passing through said nip, a system for the contactless real-time detection of said ratio of ink and dampening medium comprising, in combination,

- an ultrasonic microphone situated opposite the nip outlet, receiving sonic signals emitted in the process of said splitting occurring at the nip, and generating an electronic signal responsive to said sonic signals,
- an amplifier receiving said electronic signal generated by the ultrasonic microphone and generating a bipolar signal responsive to the electronic signal generated by the ultrasonic microphone,
- means for converting said bipolar signal of the amplifier to a unipolar signal representing the ultrasonic level, so that the unipolar signal indicates said ratio of the quantities of ink and dampening medium.

11. The combination as claimed in claim 10, wherein the offset printing machine has an inking unit, a dampening unit, and a plate cylinder, the inking and dampening units being associated with the plate cylinder, and said inking and dampening units are capable of being adjusted to regulate the flow of ink and dampening medium to keep the unipolar signal generally constant to thereby obtain a generally constant offset printing quality.

12. The combination as claimed in claim 10, wherein the means for converting comprise a rectifier followed by a low-pass frequency filter.

13. The combination as claimed in claim 11, wherein the means for converting comprise a rectifier followed by a low-pass frequency filter.

14. The combination as claimed in claim 10 wherein the frequency response of the ultrasonic microphone in combination with the amplifier has a resonant peak at a sonic frequency of approximately 40 KHz so that disturbing machine noise below 40 KHz is substantially eliminated.

15. The combination as claimed in claim 11 wherein the frequency response of the ultrasonic microphone in combination with the amplifier has a resonant peak at a sonic frequency of approximately 40 KHz so that disturbing machine noise below 40 KHz is substantially eliminated.

16. The combination as claimed in claim 10, further comprising a Fourier analyzer.

17. The combination as claimed in claim 16 wherein the frequency response of the ultrasonic microphone in combination with the amplifier is substantially flat up to approximately 100 KHz.

18. A contactless measuring method for the real-time detection of liquid properties, said method comprising the steps of:

(a) introducing a volume of the liquid into a force field, the force field effecting the separation and splitting of the volume of liquid into sub-volumes, said separation and splitting causing the emission of sonic waves, (b) receiving with an acoustic sensor the sonic waves emitted during the separation and splitting process, said acoustic sensor generating an electrical signal responsive to said sonic waves, and (c) evaluating said electrical signal by measurement.

19. The method as claimed in claim 18 wherein the acoustic sensor is tuned to ultrasonic frequencies and the step (c) of evaluating comprises measurement of the acoustic level received by the sensor.

20. The method as claimed in claim 18 wherein the step (c) of evaluating comprises Fourier analysis of the acoustic level received by the acoustic sensor.

* * * * *